US00PP21469P2

(12) United States Plant Patent
Kordes

(10) Patent No.: US PP21,469 P2
(45) Date of Patent: Nov. 16, 2010

(54) MINIATURE ROSE PLANT NAMED 'KORSMISU'

(50) Latin Name: *Rosa hybrida*
Varietal Denomination: KORsmisu

(75) Inventor: Wilhelm Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/583,069

(22) Filed: Aug. 12, 2009

(51) Int. Cl.
*A01H 5/00* (2006.01)

(52) U.S. Cl. ..... Plt./118

(58) Field of Classification Search ..... Plt./118
See application file for complete search history.

*Primary Examiner*—Susan B McCormick Ewoldt

(57) ABSTRACT

A new and distinct variety of miniature rose with long lasting, novel yellow flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Genus, species and variety denomination: The botanical classification of the new rose plant is *Rosa hybrida,* 'KORsmisu'.

BACKGROUND OF THE INVENTION

The new variety of rose plant of the present invention originated from a controlled crossing made in a rose breeding program between 'KORmispag', a non-patented rose and 'KORspunty', a patented rose described and illustrated in U.S. Plant Pat. No. 17,402 issued on Feb. 6, 2007.

The controlled crossing was made during the summer of 2004. The resulting seeds were planted in a glasshouse during the following winter, subsequently germinated and grew. Evaluations and observations were made on the resulting seedlings in a controlled environment in Offenseth-Sparrieshoop, Germany. The resulting seedlings exhibited distinctive physical and biological characteristics. The new rose plant was selected as a single plant from the seedling beds due to its superior characteristics and asexually propagated for further evaluation. This new rose plant 'KORsmisu' was selected in May 2005 from the seedling beds to be asexually propagated for further evaluation. The first asexual reproduction of 'KORsmisu' was done by rooting softwood cuttings in August, 2005 at the inventor's nursery in Offenseth-Sparrieshoop, Germany.

These initial and other subsequent propagations conducted in controlled environments demonstrate that 'KORsmisu' reproduces true to type in successive generations of asexual reproduction.

SUMMARY OF THE INVENTION

The new rose plant may be distinguished from its seed parent, 'KORmispag' by the following combination of characteristics:

1. The flower size of the seed parent is small, while the flower size of 'KORsmisu' is medium.
2. The growth habit of the seed parent is compact, while the growth habit of 'KORsmisu' is medium.

The new rose plant may be distinguished from its pollen parent, 'KORspunty' by the following combination of characteristics:

1. The growth habit of the pollen parent is vigorous, while the growth habit of 'KORsmisu' is moderate.
2. Flower buds and flowers are typically borne in clusters for the pollen parent, while borne singularly for 'KORsmisu'.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORsmisu' from all other varieties of which we are aware.

BRIEF DESCRIPTION OF THE DRAWING

The accompanying drawing shows as true as is reasonably possible to obtain in color photographs of this type, the typical characteristics of the buds, flowers, reproductive organs, leaves, juvenile foliage, and stems of 'KORsmisu'.

DETAILED BOTANICAL DESCRIPTION

The following is a description of 'KORsmisu', as observed in its growth in January, 2009 in a nursery in Jackson County, Oreg. on plants of three months of age. Color references are made using The Royal Horticultural Society (London, England) Colour Chart, 2001 except where common terms of color are used.

For a comparison, several physical characteristics of the rose variety 'KORamgat', a rose variety from the same inventor described and illustrated in U.S. Plant Pat. No. 15,612 and issued on Mar. 1, 2005 are compared to 'KORsmisu' in Chart 1.

CHART 1

| | 'KORsmisu' | 'KORamgat' |
|---|---|---|
| Petal color: upon opening, innermost petals | Outer side: Yellow Group 13B. Inner side: Yellow Group 9A. | Outer side: Yellow Group 13B. Inner side: Yellow Group 13B. |
| Petal color: upon opening, outermost petals | Outer side: Yellow Group 9A. Inner side: Yellow Group 9A. | Outer side: Yellow Group 6C. Inner side: Yellow Group 6B |
| Petal base | No distinctive coloration. | No distinctive coloration. |

Parents:

*Seed parent.*—'KORmispag'.

*Pollen parent.*—'KORspunty'.

Classification:

*Botanical classification.*—*Rosa hybrida,* 'KORsmisu'.

*Commercial classification.*—Miniature rose.

FLOWER AND FLOWER BUD

Blooming habit: Recurrent.

*Flower bud.*—Size: Upon opening, 28-30 mm in length from base of receptacle to end of bud and 18-20 mm in diameter at its widest point. Bud form: Long. Pointed ovoid.

*Bud color.*—As sepals first unfold, bud color is Green-Yellow Group 1A. When ¼ open, the upper surface of petals is Yellow Group 9A, and the lower surface is Yellow Group 9A. Guard petals are Yellow-Green Group 154B.

*Sepals.*—Size: Average 25-30 mm long×5-7 mm wide. Shape: Sepals generally subulate. Sepal apex is generally cirrose. Moderate foliaceous appendages on three of the five sepals. Base is flat at union with receptacle. Quantity: Five. Margins: With fine white hairs and a few stipitate glands. Surface texture: Inner side: Covered in fine white hairs. Outer surface: Smooth. Color: Upper surface Green Group 137B. Lower surface Green Group 137A.

Receptacle:

*Surface.*—Smooth.

*Color.*—Yellow-Green Group 144A.

*Shape.*—Funnel shaped.

*Size.*—7-8 mm (h)×6-7 mm (w).

Peduncle:

*Surface.*—With fine hairs and stipitate glands.

*Length.*—30-35 mm average length.

*Diameter.*—2.0 to 2.5 mm average diameter.

*Color.*—Yellow-Green Group 144A.

*Strength.*—Somewhat strong.

*Borne.*—Singly. 1 - 3 buds per flowering stem.

Flower bloom:

*Fragrance.*—Very light.

*Duration.*—Long lasting. A blooming plant with flowers has a commercial shelf life of 10-12 days. The blooms have a duration on the plant of approximately 12-14 days.

*Size.*—Large for a 10 cm pot rose. Average flower diameter is 50 mm when open. Average flower depth is 25 mm.

*Form.*—Shape of flower when viewed from the side: Upon opening, upper part: Flattened convex. Upon opening, lower part: Flat. Open flower, upper part: Flattened convex. Open flower, lower part: Concave.

Color:

*Upon opening, petals.*—Outermost petals: Outer Side: Yellow Group 9A. Inner Side: Yellow Group 9A. Innermost petals: Outer Side: Yellow Group 13B. Inner Side: Yellow Group 9A. No distinctive coloration at petal base observed.

*After opening, petals.*—Outermost petals: Outer Side: Yellow Group 12A. Inner Side: Yellow Group 9A. Innermost petals: Outer Side: Yellow Group 13B. Inner Side: Yellow Group 9A. No distinctive coloration at petal base observed.

*Variegations.*—None.

General tonality: On open flower Yellow Group 13B. No change in the general tonality at the end of the 9th day. Afterwards, general tonality is 13C.

Petals:

*Petal count.*—Approximately 50-60 petals under normal conditions.

*Petal reflex.*—Petals reflex slightly.

*Petal edge.*—Entire. With small point in center of margin.

*Petal shape.*—Deltoid. Apex shape is round. Shape of base is acute.

*Petal size.*—25-27 mm long; 22-24 mm wide.

*Thickness.*—Average.

*Petal arrangement.*—Generally in a regular pattern with overlapping edges.

Petaloids: Present.

*Petaloid count.*—Average of 10-15 per flower.

*Petaloid edge.*—Smooth.

*Petaloid texture.*—Smooth.

*Petaloid shape.*—Oblanceolate.

*Petaloid size.*—Petaloids are 10-15 mm long and 6-10 mm wide.

*Petaloid color.*—Color of inner side is Yellow Group 9A. Color of outer side is Yellow Group 13B.

Reproductive organs: Flowers are incomplete, lacking complete pistils. The incomplete parts are narrow appendages with coloration of Yellow-Green Group 145C. These incomplete floral parts have flat bases at the point of attachment and are narrow with a tapered apex. These incomplete floral pistils are 5-7 mm (l)×1-1.5 mm (w).

*Stamens.*—Approximately 3-4 on average and regularly arranged. Anthers: Size: 2-3 mm long. Color: Green-Yellow Group 1B. Pollen: Absent. Filaments: Color: Yellow Group 3A. Length: 3 mm.

THE PLANT

*Plant growth.*—Moderate vigor. Compact and uniform habit. When grown as 10 cm pot plant, the average height of the plant itself is 25-30 cm and the average width is 20-25 cm.

*Stems.*—Stem color: Young wood: Yellow-Green Group 144A. Older wood: Yellow-Green Group 146B. Stem surface: Young wood: Smooth. Older wood: Smooth.

*Prickles.*—Present Incidence: 1-3 per 10 cm of stem. Size: Average length: 4 mm. Color: Immature prickles: Greyed-Yellow Group 161B. Mature prickles: Greyed-Orange Group 177C. Senescing to Greyed-Orange Group 177A. Shape: Linear.

*Leaves and leaflets.*—Normally 3-5 leaflets on normal leaves in middle of the stem. Venation pattern: Pyramidal net pattern. Leaf size: 90-95 mm (l)×60-65 mm (w). Quantity: Abundant. Texture: Upper side of leaflet: Glossy. Smooth. Under side of leaflet: Matte. Rough. Color, mature foliage: Upper Leaf Surface: Green Group 139A. Lower Leaf Surface: Green Group N138C. Color, juvenile foliage: Upper Leaf Surface: Green Group 139A. Lower Leaf Surface: Green Group N138C. Anthocyanin intonation: Present. Location: intonations present on leaf margins and developing leaves of plants grown under high light conditions.

*Stipules.*—Size: 12-16 mm long. 8 mm between the tips of the stipule. Main body of stipule 4 mm in width. Shape: Longitudinally flanged or winged along middle. Stipule color: Green Group 137A and Yellow Green Group 144B. Anthocyanin Greyed-Purple Group 184B. Presence of stipitate glands: Present on margins. Margins: Serrated. With stipitate glands.

*Petiole.*—Length: 12-15 mm. Diameter: 1-1.5 mm. Petiole color: Green Group 137A. Anthocyanin present on juvenile tissue. Greyed-Purple Group 184B. Underneath: A few small prickles underneath. Stipitate glands: Limited numbers of stipitate glands on margins.

*Petiole rachis.*—Length: 12-13 mm. Diameter: 1-1.5 mm. Color: Green Group 137A. Anthocyanin present on juvenile tissue. Greyed-Purple Group 184B. Prickles: A few small prickles underneath. Stipitate glands: Limited numbers of stipitate glands on margins.

*Leaflets.*—Size: Average size of the terminal leaflet is 50 mm (l)×32 mm (w). Shape: Ovate. Base: Ovate. Apex: Acute. Surface: Upper side: Glossy. Lower side: Matte. Margins: Serrated. Texture: Thin.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to Powdery mildew (*Sphaerotheca pannosa*) and *Botrytis* (*Botrytis cinerea*) diseases under normal growing conditions.

I claim:

1. A new and distinct variety of miniature rose plant characterized by the following combination of characteristics:

(a) Forms abundant, attractive long lasting yellow flowers;

(b) Exhibits a compact and bushy growth habit;

(c) Is suited for growing in greenhouse in pots from softwood cuttings, and;

(d) Exhibits durable flowers and foliage suitable for distribution in the floral industry; substantially as herein illustrated and described.

* * * * *

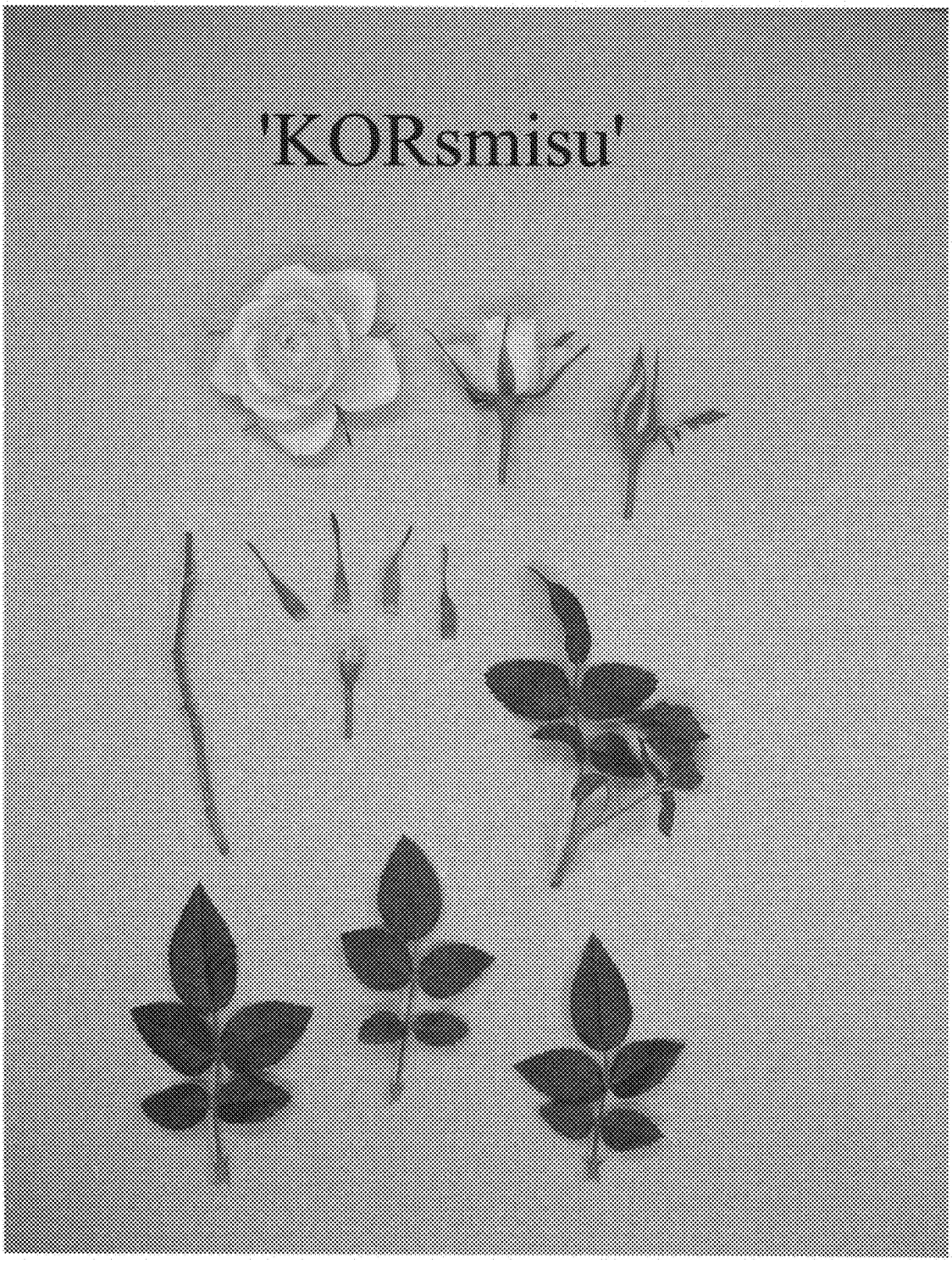
'KORsmisu'